United States Patent
Koganei et al.

(10) Patent No.: US 11,452,743 B2
(45) Date of Patent: Sep. 27, 2022

(54) METALLIC COPPER FINE PARTICLES AND METHOD FOR PRODUCING THE SAME

(71) Applicant: TOYO SEIKAN GROUP HOLDINGS, LTD., Tokyo (JP)

(72) Inventors: Akiko Koganei, Yokohama (JP);
Kazuaki Ohashi, Yokohama (JP);
Yasuhiro Kosaka, Yokohama (JP);
Daisuke Ikutame, Yokohama (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 34 days.

(21) Appl. No.: 16/753,068

(22) PCT Filed: Oct. 2, 2018

(86) PCT No.: PCT/JP2018/036924
§ 371 (c)(1),
(2) Date: Apr. 2, 2020

(87) PCT Pub. No.: WO2019/069942
PCT Pub. Date: Apr. 11, 2019

(65) Prior Publication Data
US 2020/0289556 A1 Sep. 17, 2020

(30) Foreign Application Priority Data

Oct. 3, 2017 (JP) .............. JP2017-193707
Oct. 3, 2017 (JP) .............. JP2017-193708

(51) Int. Cl.
*A61K 33/34* (2006.01)
*B22F 1/02* (2006.01)
(Continued)

(52) U.S. Cl.
CPC ............ *A61K 33/34* (2013.01); *A61K 9/5015* (2013.01); *A61P 31/12* (2018.01); *B22F 1/054* (2022.01);
(Continued)

(58) Field of Classification Search
None
See application file for complete search history.

(56) References Cited

U.S. PATENT DOCUMENTS

| 4,350,535 A | * | 9/1982 | Ishijima | ............... C09D 17/006 106/403 |
| 6,294,186 B1 | * | 9/2001 | Beerse | ................... A61P 11/00 424/405 |

(Continued)

FOREIGN PATENT DOCUMENTS

| CN | 102015614 A | 4/2011 |
| CN | 102307934 A | 1/2012 |

(Continued)

OTHER PUBLICATIONS

Communication dated Jul. 27, 2021 from The State Intellectual Property Office of P.R. of China in corresponding Application No. 201880065000.6.

(Continued)

*Primary Examiner* — Alexandre F Ferre
(74) *Attorney, Agent, or Firm* — Sughrue Mion, PLLC (57) ABSTRACT

Metallic copper fine particles coated with a fatty acid and an ester compound. Also disclosed is an antiviral agent containing the metallic copper fine particles and a method for producing the metallic copper fine particles.

15 Claims, 1 Drawing Sheet

(51) Int. Cl.
  *B22F 1/00* (2022.01)
  *A61K 9/50* (2006.01)
  *A61P 31/12* (2006.01)
  *B22F 1/16* (2022.01)
  *B22F 1/054* (2022.01)

(52) U.S. Cl.
  CPC ............ *B22F 1/16* (2022.01); *B22F 2301/10* (2013.01); *B22F 2304/054* (2013.01); *B22F 2304/056* (2013.01); *B22F 2304/058* (2013.01)

(56) References Cited

U.S. PATENT DOCUMENTS

| | | | |
|---|---|---|---|
| 8,889,164 B2 | 11/2014 | Hashimoto et al. | |
| 2008/0171090 A1* | 7/2008 | Yagi | A61K 31/7088 424/490 |
| 2014/0127321 A1 | 5/2014 | Kurahashi et al. | |
| 2016/0090345 A1 | 3/2016 | Ohashi et al. | |
| 2016/0255841 A1* | 9/2016 | Ohashi | A01N 59/16 |
| 2019/0098902 A1 | 4/2019 | Ogata et al. | |

FOREIGN PATENT DOCUMENTS

| | | | |
|---|---|---|---|
| CN | 103044945 A | 4/2013 | |
| CN | 103649230 A | 3/2014 | |
| CN | 104276940 A | 1/2015 | |
| JP | 2005-298921 A | 10/2005 | |
| JP | 2013-082654 A | 5/2013 | |
| JP | 5194185 B1 | 5/2013 | |
| JP | 2015-205998 A | 11/2015 | |
| KR | 10-2016-0075634 A | 6/2016 | |
| WO | 2010/055944 A1 | 5/2010 | |
| WO | WO-2014091861 A1 * | 6/2014 | ............ A01N 25/22 |
| WO | WO-2015064700 A1 * | 5/2015 | ............ B22F 1/0022 |
| WO | 2017/170593 A1 | 10/2017 | |

OTHER PUBLICATIONS

Communication dated Jan. 21, 2021, from the Korean Intellectual Property Office in application No. 10-2020-7011608.
International Search Report for PCT/JP2018/036924 dated Oct. 30, 2018 [PCT/ISA/210].

* cited by examiner

METALLIC COPPER FINE PARTICLES AND METHOD FOR PRODUCING THE SAME

CROSS REFERENCE TO RELATED APPLICATIONS

This application is a National Stage of International Application No. PCT/JP2018/036924 filed Oct. 2, 2018, claiming priority based on Japanese Patent Application No. 2017-193707 filed Oct. 3, 2017 and Japanese Patent Application No. 2017-193708 filed Oct. 3, 2017.

TECHNICAL FIELD

The present invention relates to metallic copper fine particles, an antiviral agent containing the metallic copper fine particles, and a method for producing the same.

BACKGROUND ART

In conventional techniques, silver ions or copper (II) ions are used as active ingredients for antibacterial or antiviral materials. Various antiviral materials have been proposed, and the materials are prepared by allowing these metal ions to be supported by substances such as zeolite and silica gel, or by dispersing the metal ions in a solvent.

The metal ions can exhibit antiviral activity against viruses like influenza virus that have an envelope structure. However, the metal ions cannot exhibit the antiviral activity against viruses like norovirus that have no envelope structure.

A monovalent copper compound is also known as a metal compound that can exhibit antiviral activity regardless of presence or absence of an envelope structure. For instance, Patent document 1 below describes an antiviral composition. The composition contains monovalent copper compound fine particles, a reducing agent and a dispersion medium, and it has pH of 6 or lower. Patent document 2 below describes an antibacterial and antiviral composition containing cuprous oxide particles having a BET specific surface area of 5 to 100 $m^2/g$, saccharides having aldehyde groups, and a photocatalytic substance. And Patent document 3 below describes an antiviral coating having a copper supporting oxide, barium sulfate and a water-repellent resin binder. The copper supporting oxide includes oxide particles supporting at least either copper particles or copper compound particles and it has an average secondary particle diameter of 80 nm to 600 nm. The barium sulfate has an average secondary particle diameter of 1 μm to 15 μm.

PRIOR ART DOCUMENTS

Patent Documents

[Patent Document 1] Japanese Patent No. 5194185
[Patent Document 2] Japanese Publication No. 2013-82654
[Patent Document 3] Japanese Publication No. 2015-205998

SUMMARY OF THE INVENTION

Problems to be Solved by the Invention

However, the monovalent copper compound fine particles may aggregate easily, and it may be difficult to disperse the monovalent copper compound homogeneously. In a case of using the dispersion liquid as an antiviral composition or in a case of mixing with a coating material to provide a coated antiviral article, it is difficult for the monovalent copper compound fine particles to efficiently exhibit the antiviral activity.

The above-identified patent documents refer to monovalent copper compounds with larger particle diameters. When the monovalent copper compound is used, the particle surface area is decreased to reduce the opportunity of contact with the viruses, thereby degrading the antiviral activity. In a case of an antiviral article coated with the monovalent copper compound having a larger particle diameter, the haze or the optical transmittance may deteriorate to impair the transparency.

The monovalent copper compound fine particles can be obtained by pulverization, but the particles may easily aggregate due to absence of coating agent or stabilizer, and this may accelerate oxidation to change cuprous oxide to copper (II) oxide.

In order to solve these problems, the present inventors suggested, in Japanese Patent Application No. 2016-247641, monovalent copper compound particles that can exhibit efficiently the antiviral activity and a dispersion liquid containing the same. The present inventors further continued eagerly their research on the fine particles capable of exhibiting more efficiently a higher antiviral activity, so that the present inventors found that metallic copper can exhibit an antiviral activity superior to that of a monovalent copper compound.

Therefore, an object of the present invention is to provide fine particles of a metallic copper compound capable of exhibiting the antiviral activity efficiently, and a method for producing the metallic copper fine particles.

Means for Solving the Problems

The present invention provides metallic copper fine particles, which are coated with a fatty acid and an ester compound.

It is preferable in the metallic copper fine particles of the present invention that:
1. the ester compound is an ester compound of a fatty acid and polyol
2. the fatty acid is a higher fatty acid having a carbon number of 10 to 22; and
3. the average particle diameter is in a range of 10 to 500 nm.

The present invention further provides an antiviral agent containing the metallic copper fine particles.

It is preferable in the antiviral agent of the present invention that:
1. the antiviral agent includes a dispersion liquid containing the metallic copper fine particles dispersed in a solvent;
2. the antiviral agent includes a resin composition containing the metallic copper fine particles dispersed in a resin;
3. the antiviral agent contains the metallic copper fine particles in an amount of 0.05 to 2.0% by weight, and has an antiviral activity value of not less than 3.0;
4. the antiviral agent containing the metallic copper fine particles in an amount of 0.05 to 2.0% by weight in terms of metallic copper, and generates superoxide anion radical in an amount of not less than 5000 counts/mL by a reaction with MPEC when the amount of the radical is expressed as a luminescence amount by chemiluminescence; and
5. the antiviral agent containing the metallic copper fine particles has a protein decrease rate of not less than 10% in a measurement by the BSA method.

The present invention provides further a method for producing metallic copper fine particles. The method includes steps of: introducing fatty acid copper into polyol and heat-mixing to prepare a dispersion liquid containing metallic copper fine particles coated at least with the fatty acid; mixing the dispersion liquid with a low-boiling point solvent that contains a dispersing agent and an ester compound; and separating the polyol and the low-boiling point solvent into two phases and extracting the metallic copper fine particles coated with the fatty acid and the ester compound from the polyol into the low-boiling point solvent (hereinafter, this may be called "first production method").

The present invention provides further a method for producing metallic copper fine particles. The method includes steps of: introducing a fatty acid and a copper compound into polyol and heat-mixing to prepare a dispersion liquid containing metallic copper fine particles coated at least with the fatty acid; mixing the dispersion liquid with a low-boiling point solvent that contains a dispersing agent and an ester compound; and separating the polyol and the low-boiling point solvent into two phases and extracting the metallic copper fine particles coated with the fatty acid and the ester compound from the polyol into the low-boiling point solvent (hereinafter, this may be called "second production method").

It is preferable in the first or second method for producing metallic copper fine particles that:
1. the copper compound is selected from the group consisting of copper acetate, copper chloride, and copper bromide;
2. the low-boiling point solvent containing the extracted metallic copper fine particles is volatilized;
3. the ester compound is an ester compound of the fatty acid and polyol;
4. the low-boiling point solvent is selected from the group consisting of butyl acetate, ethyl acetate, and methyl isobutyl ketone; and
5. the polyol is selected from the group consisting of diethylene glycol, ethylene glycol, triethylene propylene glycol, and glycerol.

The present invention provides further a method for producing metallic copper fine particles. The method includes a step of incorporating fatty acid copper into polyol and heating at a temperature lower than the thermal decomposition starting temperature of the fatty acid copper so as to form the metallic copper fine particles in the polyol (hereinafter, this may be called "third production method").

It is preferable in the third method for producing metallic copper fine particles that the polyol is selected from the group consisting of diethylene glycol, ethylene glycol, triethylene glycol, propylene glycol, and glycerol.

Effect of the Invention

The metallic copper fine particles of the present invention have properties such as antiviral activity, antibacterial activity, electric conductivity, ultraviolet shielding property, and antifouling property. In particular, the copper fine particles can exhibit antiviral activity regardless of presence or absence of an envelope structure, and thus, it can exhibit antiviral activity even against viruses like norovirus that do not have an envelope structure. Though the monovalent copper compound particles exhibit similar effects, the metallic copper fine particles can exhibit an antiviral activity superior to that of the monovalent copper compound particles.

Further, since the surfaces of the metallic copper fine particles are coated with the fatty acid and an ester compound, the metallic copper fine particles are prevented from oxidation and aggregation, and thus, the particles can exhibit excellent antiviral activity for a long time period.

Furthermore, the metallic copper fine particles coated with the fatty acid and the ester compound can be dispersed without aggregation even when they are contained at a high concentration in a non-aqueous solvent such as a low-boiling point solvent. And thus, the metallic copper fine particles can exhibit efficiently favorable properties even in a dispersion liquid. Therefore, the particles can be used favorably in a form of a dilution solvent for a coating composition and resin composition in order to impart various properties to the coating or the resin articles.

In a case where metallic copper fine particles coated with the fatty acid and the ester compound are blended in a resin composition, a direct contact between the metallic copper fine particle surfaces and the resin is reduced. This can decrease effectively decomposition of the resin and reduce lowering of the molecular weight of the resin, for instance. As a result, this can prevent effectively impairment in the formability and processability. Further, the metallic copper fine particles are provided uniformly and stably on the surface of an article so as to impart the article with an excellent antiviral activity for a long period of time.

The metallic copper fine particles of the present invention having a small primary particle diameter of 10 to 500 nm in average can generate active oxygen efficiently, and thus, the particles can exhibit excellent antiviral activity.

The metallic copper fine particles of the present invention may be used in a form of a dispersion liquid containing the metallic copper fine particles, and the dispersion liquid may be used as a diluent for a resin composition that constitutes textiles or the like, or the dispersion liquid may be coated directly on or impregnated into textiles or the like. The dispersion liquid may be mixed with a binder resin and coated on textiles or the like. In this way, the textiles or the like can be imparted with antiviral activity.

Further, the dispersion liquid containing the metallic copper fine particles of the present invention may be mixed with a coating material and coated on a film, sheet or a metal substrate, thereby imparting surfaces or outer faces of substrates with antiviral activity.

In each of the first and second method for producing the metallic copper fine particles of the present invention, fatty acid copper is blended in polyol, or a fatty acid and a copper compound are blended in polyol, and the blend is heated so that the monovalent or divalent copper is reduced to a metallic copper, and thus, metallic copper fine particles may be formed easily. At the same time, this process makes it possible to form metallic copper fine particles on which the fatty acid and the ester compound, preferably a fatty acid and the ester compound of the fatty acid, are coordinated. Since the metallic copper fine particles exhibit excellent compatibility with a low-boiling point solvent, the metallic copper fine particles can be extracted from the polyol into the low-boiling point solvent efficiently in a simple manner, and the metallic copper fine particles can be contained at a high concentration in the low-boiling point solvent.

It is also possible to separate easily the metallic copper fine particles by volatilizing the low-boiling point solvent that contains the metallic copper fine particles at a high concentration.

In the third method for producing the metallic copper fine particles of the present invention, fatty acid copper is blended in polyol and heated, whereby a monovalent or divalent copper compound is reduced to metallic copper. At the same time, a fatty acid and an ester compound of the fatty acid and polyol are coordinated on the surfaces of the thus formed metallic copper fine particles. In this manner, metallic copper fine particles having excellent antiviral activity can be formed in the polyol.

MODE FOR CARRYING OUT THE INVENTION (Metallic Copper Fine Particles)

In the metallic copper fine particles of the present invention, the metallic copper as the active ingredient to exhibit the antiviral activity is capable of adsorbing and inactivating viruses, and thus, it can exhibit excellent antiviral activity regardless of presence or absence of an envelope structure.

It is considered that the excellent antiviral activity of the metallic copper fine particles of the present invention is exhibited in the following manner. That is, active oxygen generated from the metallic copper has oxidizing power to denature the protein of the virus including micro protein. In addition to that, the metallic copper reacts with a thiol group of the protein of the virus so as to denature the protein, whereby the virus is inactivated.

In the present invention, it is preferable that the surfaces of the metallic fine particles are coated with a fatty acid and an ester compound. Though enhancement of the surface activity of the metallic copper fine particles may cause oxidation of the fine particle surface, the coating can prevent the oxidation, and at the same time can prevent or decrease aggregation of the fine particles, thereby exhibiting the excellent antiviral activity for a long period of time.

The metallic copper fine particles of the present invention possess not only the antiviral activity but antibacterial activity, electric conductivity, ultraviolet shielding property, antifouling property and the like.

Examples of the fatty acid to coat the metallic copper fine particle surface include myristic acid, stearic acid, oleic acid, palmitic acid, n-decanoic acid, paratoylic acid, succinic acid, malonic acid, tartaric acid, malic acid, glutaric acid, adipic acid, and acetic acid. These can be combined with at least one of the others, and the preferred examples include higher fatty acids having 10 to 22 carbon atoms, particularly, stearic acid.

The ester compound to coat the metallic copper fine particle surface may be an ester compound to be blended in the low-boiling point solvent, or it may include an ester compound derived from the fatty acid and polyol as the raw materials. These may be ester compounds different from each other, but the ester compound to be blended in the low-boiling point solvent is preferably the same type of the ester compound derived from the raw materials.

Examples of the preferred ester compound to coat the metallic copper fine particle surface include an ester compound of the aforementioned fatty acid and the ester compound of the below-mentioned polyol, such as diethylene glycol distearate, ethylene glycol distearate, and propylene glycol distearate, though the present invention is not limited to these examples.

In the present invention, the metallic copper fine particles have an average primary particle diameter preferably in a range of 10 to 500 nm, and particularly preferably 10 to 200 nm. When the average primary particle diameter of the metallic copper fine particles is within the range, the excellent antiviral activity can be exhibited efficiently. Namely, the metallic copper fine particles having a smaller average primary particle diameter may be brought into contact more with the oxygen, they can generate active oxygen efficiently to exhibit excellent antiviral activity. In calculation of the average particle diameter in the present Description, a plurality of copper fine particles having no space therebetween are regarded as constituting one particle.

The metallic copper fine particles of the present invention can be obtained in various embodiments. For instance, the metallic copper fine particles can be provided in the form of a dispersion liquid obtained by the first or second production method described below, namely, the metallic copper fine particles are dispersed in a low-boiling point solvent to form a dispersion liquid. In another dispersion liquid obtained by the third production method, the metallic copper fine particles are dispersed in polyol. In alternative use embodiments, the solvent can be removed from the dispersion liquid to obtain a paste, or the metallic copper fine particles can be provided as a dry powder. Among them, the dispersion liquid is particularly preferred since it can be obtained directly by the production method mentioned below, and can be handled easily to impregnate the textile, or it can be used as a diluent or the like for the resin composition. The metallic copper fine particles are contained in the dispersion liquid in an amount of 0.01 to 2% by weight and particularly in an amount of 0.05 to 1% by weight so that sufficient antiviral activity can be imparted by use of a moderate quantity of dispersion liquid.

Examples of the dispersion medium in the dispersion liquid include low-boiling point solvents: esters such as methyl acetate, ethyl acetate and butyl acetate; hydrocarbons such as hexane, heptane, toluene, xylene and cyclohexane; and ketones such as methyl isobutyl ketone, methyl ethyl ketone and cyclohexanone. Among them, the ester-based solvents are preferred, and butyl acetate is preferred particularly. Since the dispersion medium is a non-aqueous low-boiling point solvent, it can be used effectively as a diluent for hydrophobic coating compositions and resin compositions.

The paste of the metallic copper fine particles is obtained by preparing a dispersion liquid by the production method as described below, where metallic copper fine particles are dispersed in a low-boiling point solvent, and then by dry-solidifying the dispersion liquid. The thus obtained metallic copper fine particles can be re-dispersed in a fluid like water such as purified water and ion exchange water; lower alcohols such as methanol, ethanol, propanol, isopropanol, and butanol; and ordinary denatured alcohols, which are denatured with methanol, benzol, triol, methyl ethyl ketone, denatonium benzoate, fragrance and the like.

The dispersion liquid preferably contains a dispersing agent in addition to the metallic copper fine particles, whereby the metallic copper fine particles can be dispersed homogeneously in the dispersion liquid even when the particles are contained at a high concentration. Examples of preferred dispersing agents will be described below.

Further, conventionally known additives can be blended in the dispersion liquid in accordance with conventionally known formula. Examples of the additives include an antioxidant, an ultraviolet absorber, an antistatic agent, and a dye.

(Antiviral Agent)

The present invention further provides an antiviral agent containing the metallic copper fine particles.

The antiviral agent of the present invention can be used in various forms as long as its active ingredient is metallic copper. Preferably, it is provided in a form of the metallic copper fine particles, a dispersion liquid containing the metallic copper fine particles dispersed in a solvent, or a resin composition containing the metallic copper fine particles dispersed in a resin.

The antiviral activity of the antiviral agent of the present invention can be evaluated by the methods mentioned below.

Specifically, the antiviral agent of the present invention contains the metallic copper fine particles in an amount of 0.05 to 2.0% by weight. This antiviral agent has an antiviral activity value of not less than 3.0 in a measurement in Examples described below, even with respect to the influenza virus having an envelope structure, and further feline calicivirus as a surrogate for norovirus having no envelope structure.

The amount of superoxide anion radical generated from the antiviral agent is represented as luminescence measured by chemiluminescence method by a reaction with MPEC (2-methyl-6-p-methoxyphenylethynylimidazopyrazinone). For the antiviral agent of the present invention containing the metallic copper fine particles in an amount of 0.05 to 2.0% by weight in terms of metallic copper, the luminescence is not less than 5000 counts/mL. The antiviral agent can generate a large amount of the active oxygen species efficiently, exhibiting excellent antiviral activity.

Furthermore, the antiviral agent of the present invention, which contains the metallic copper fine particles, has a protein decrease rate of not less than 10% in a measurement by the BSA method (reaction with 0.2 ml of BSA solution (50 μg/mL)). That is, the antiviral agent of the present invention having excellent antiviral activity can denature efficiently the protein constituting the virus and inactivate the virus.

(First Production Method)

The metallic copper fine particles of the present invention can be prepared by the method described below.

(1) First Step

Fatty acid copper is incorporated into polyol and heated so as to prepare a polyol dispersion liquid containing metallic copper fine particles whose surfaces are coated on the surfaces with the fatty acid. Here, it is further preferable that the surfaces of the metallic copper fine particles are coated with not only the fatty acid but an ester compound of the fatty acid and polyol.

The heating temperature is preferably lower than the decomposition starting temperature for the fatty acid copper in use, specifically in a range of 160 to 230° C. The time for heating and mixing is preferably 60 to 360 minutes.

The amount of the fatty acid copper to be blended is preferably 0.1 to 5 parts by weight per 100 parts by weight of the polyol. When the amount of the fatty acid copper is less than the above-described range, sufficient antiviral activity may not be imparted to the dispersion liquid in comparison with a case where the amount is within the range. When the amount of the fatty acid copper is more than the above-described range, the economic efficiency may be inferior and at the same time the coating ability and formability may be impaired in comparison with a case where the amount is within the range.

Examples of the polyol include ethylene glycol, diethylene glycol, triethylene glycol, polyethylene glycol, and glycerol. They can be selected considering the combination with the low-boiling point solvent described below.

(2) Second Step

Next, the polyol dispersion liquid and a low-boiling point solvent are mixed to prepare a mixture. Here, the polyol dispersion liquid contains the metallic copper fine particles dispersed therein and coated with a fatty acid, or preferably a fatty acid and an ester compound of the fatty acid. The low-boiling point solvent contains a dispersing agent and an ester compound which are blended therein in advance.

The low-boiling point solvent in an amount of 10 to 200 parts by weight is preferably incorporated into the polyol dispersion liquid of 100 parts by weight.

For the low-boiling point solvent, the low-boiling point solvents applicable to the aforementioned dispersion liquids can be used. Among them, butyl acetate, ethyl acetate, and methyl isobutyl ketone can be used preferably. The low-boiling point solvent is required to be incompatible with the polyol, and thus, the polyol and the low-bowling point solvent are combined preferably so that the difference in the solubility parameter (Sp value) becomes 3 or more.

It is preferable that butyl acetate (Sp value: 8.4) is used as the low-boiling point solvent when diethylene glycol (Sp value: 12.6) is used as the polyol.

The blend amount, of the dispersing agent in the low-boiling point solvent may vary depending on the amount of the metallic copper fine particles dispersed in the polyol dispersion liquid and coated with a fatty acid, or preferably a fatty acid and an ester compound of the fatty acid. Preferably, the amount is in a range of 0.01 to 2 parts by weight per 100 parts by weight of the low-boiling point solvent.

An example of applicable dispersing agent is a polymeric dispersing agent having on its adsorption group at least one of primary, secondary or tertiary amine or an amine salt neutralized with the counter ion, carboxylic acid or carboxylate salt, or hydroxyl group, and having on its main chain or side chain any of a fatty acid, polyether, polyester, polyurethane, or polyarylate.

These dispersing agents having adsorption groups adsorb on the surfaces of the metallic copper fine particles, and improve the compatibility with the non-aqueous solvent by use of the main chain or the side chain. As a result, repulsive force due to steric hindrance of the polymer chain is generated, aggregation of the metallic copper fine particles is prevented or decreased, and the metallic copper fine particles can be dispersed homogeneously in the non-aqueous solvent, whereby the aggregation over time can be eliminated.

The polymeric dispersing agent used here may be selected from what is composed of only a main chain, what has a comb-structure having a side chain, and what has a star-shaped structure.

The amount of the ester compound to be blended in the low-boiling point solvent may vary depending on the amount of the metal is copper fine particles in the polyol dispersion liquid, where the metallic copper fine particles are coated with a fatty acid, or preferably a fatty acid and an ester compound of the fatty acid. The amount is preferably in a range of 0.1 to 2.0 parts by weight per 100 parts by weight of the low-boiling point solvent.

As mentioned above, the ester compound to be blended in the low-boiling point solvent is preferably an ester compound of a fatty acid and polyol, and more preferably, it is an ester compound obtained from the fatty acid copper and polyol used as the raw materials. Specifically, when the polyol as the raw material is diethylene glycol and the fatty acid copper as the raw material is copper stearate, diethylene glycol distearate or ethylene glycol distearate may be blended preferably as the ester compound.

(3) Third Step

The above-described mixture is made stand still at a temperature of 0 to 40° C., for 30 to 120 minutes so as to phase-separate the polyol and the low-boiling point solvent. Due to the phase separation of the mixture, the metallic copper fine particles in the mixture, which are coated with a fatty acid and the ester compound of the fatty acid, are extracted into the low-boiling point solvent. Since the dispersing agent is blended in advance in the low-boiling point solvent, the adsorption groups of the dispersing agent are coordinated at the metallic copper fine particles to accelerate extraction of the metallic copper fine particles into the low-boiling point solvent.

Next, the polyol is eliminated from the phase-separated mixture. The thus obtained dispersion liquid contains metallic copper fine particles dispersed in the low-boiling point solvent, and the particles are coated with the fatty acid and the ester compound of the fatty acid.

The polyol can be eliminated by any of conventionally known methods, such as simple distillation, vacuum distillation, precision distillation, thin film distillation, extraction, and membrane separation.

The metallic copper fine particles may be re-dispersed the obtained dispersion liquid is subjected to a conventionally known process such as filtration, centrifugation, and volatilization to eliminate the low-boiling point solvent, thereby obtaining metallic copper fine particles in a dry state.

(Second Production Method)

The method of producing metal copper fine particles dispersed in a low-boiling point solvent and coated with a fatty acid and an ester compound of the fatty acid is not limited to the aforementioned production method. The metallic copper fine particles can be prepared by an alternative method below.

Specifically, during the first step of the aforementioned first production method, a combination of a fatty acid and a copper compound is incorporated in place of the fatty acid copper, while the remaining steps are conducted similarly to the first production method, thereby preparing a dispersion liquid containing metallic copper fine particles coated with the fatty acid, or preferably coated with the fatty acid and an ester compound of the fatty acid.

Examples of the copper compound include oxides, acetic acid compounds, chlorides, bromides, hydroxides, and cyanides. Among them, any of copper acetate, copper chloride, and copper bromide can be used particularly preferably.

(Third Production Method)

In the first step of the aforementioned first and second production methods, a dispersion liquid containing metallic copper fine particles dispersed in the polyol and coated with the fatty acid and the ester compound of the fatty acid is obtained. The dispersion liquid can be used directly in the present invention.

Specifically, fatty acid copper, or a combination of a fatty acid and a copper compound is incorporated into the polyol, which are heated and mixed to prepare a polyol dispersion liquid containing the metallic copper fine particles dispersed therein.

(Use of Metallic Copper Fine Particles)

As described above, the metallic copper fine particles of the present invention have excellent antiviral activity. Therefore, the metallic copper fine particles fixed onto the surface of an article or included in the article react with oxygen and generate active oxygen, thereby exhibiting excellent antiviral activity.

For instance, it is preferable to use the dispersion liquid containing the metallic copper fine particles as a diluent for a coating composition or a resin composition. This makes it possible to impart antiviral activity to a coating film of the coating composition or a resin article of the resin composition without impairing the transparency of the coating composition or the resin composition.

Examples of the coating composition are based on thermosetting resins such as phenolic resin, epoxy resin, urethane resin, melamine resin, urea resin, alkyd resin, unsaturated polyester resin, and silicone resin, or photo-curing acrylic resin and the like.

Examples of the resin composition include: the above-described thermosetting resins and further; olefin resins such as low-, medium-, high-density polyethylene, linear low density linear ultralow density polyethylene, isotactic polypropylene, syndiotactic polypropylene, propylene-ethylene copolymer, polybutene-1, ethylene-butene-1 copolymer, propylene-butene-1 copolymer, and ethylene-propylene-butene-1 copolymer; polyester resins such as polyethylene terephthalate, polybutylene terephthalate, and polyethylene naphthalate; polyamide resin such as nylon 6, nylon 6,6, and nylon 6,10; and thermoplastic resins such as polycarbonate resin.

Further specific examples of use include an article prepared by applying a coating composition containing an antiviral composition on a substrate such as a nonwoven fabric, a resin film or a textile. Another example thereof is an article prepared by directly shaping a resin composition containing an antiviral composition into a film, a sheet, a nonwoven fabric, a fiber and the like.

EXAMPLES

Example 1

2.5% by weight of copper stearate was incorporated into diethylene glycol, which was heated to 190° C. with stirring to obtain a diethylene glycol dispersion liquid. The heating was continued for further 2 hours, and then, the diethylene glycol dispersion liquid was cooled to 60° C.

Next, butyl acetate prepared by dissolving 1.0% by weight of DISPERBYK-2090 (manufactured by BYK Additives & Instruments) as dispersing agent and 1.0% by weight of diethylene glycol distearate were incorporated into the dispersion liquid, and the mixture was stirred. After making the mixture stand still for about 1 hour, the layer of butyl acetate was collected to prepare a (dispersion liquid of metallic copper fine particles.

Example 2

A dispersion liquid was prepared in the same manner as in Example 1 except that the heating temperature was set to 210° C.

Example 3

A dispersion liquid was prepared in the same manner as in Example 1 except that ethylene glycol distearate was used in place of the diethylene glycol distearate.

Example 4

A dispersion liquid was prepared in the same manner as in Example 1 except that copper laurate was used in place of the copper stearate.

Example 5

A dispersion liquid was prepared in the same manner as in Example 1 except that stearic acid and copper acetate were used in place of the copper stearate.

Example 6

A dispersion liquid was prepared in the same manner as in Example 1 except that ethylene glycol was used in place of the diethylene glycol.

Example 7

2.5% by weight of copper stearate was incorporated into diethylene glycol, which was heated to 190° C. with stirring to obtain a diethylene glycol dispersion liquid. The heating was continued for further 2 hours, and then, the diethylene glycol dispersion liquid was cooled to room temperature to obtain a dispersion liquid of metallic copper fine particles.

Example 8

A dispersion liquid was prepared in the same manner as in Example 7 except that glycerol was used in place of the diethylene glycol.

Example 9

A dispersion liquid was prepared by dry-solidifying the solvent of the dispersion liquid in Example 1 to obtain metallic copper fine particles, then incorporating the metallic copper fine particles into water and stirring.

Comparative Example 1

A dispersion liquid was prepared in the same manner as in Example 1 except that the diethylene glycol distearate was not incorporated into the butyl acetate.

Comparative Example 2

A dispersion liquid was prepared in the same manner as in Example 1 except that copper sulfate was used in place of the copper stearate.

Comparative Example 3

A dispersion liquid was prepared by incorporating 0.05% by weight of a metallic copper fine particle reagent (manufactured by Sigma-Aldrich, Inc.), 1.0% by weight of DISPERBYK-2090 and 1.0% by weight of diethylene glycol distearate to butyl acetate, and by stirring with an ultrasonic vibration device.

Comparative Example 4

A dispersion liquid was prepared by incorporating 0.05% by weight of a copper oxide (I) reagent, 1.0% by weight of DISPERBYK-2090 and 1.0% by weight of diethylene glycol distearate to butyl acetate, and by stirring with an ultrasonic vibration device.

Comparative Example 5

A dispersion liquid was prepared by incorporating 0.05% by weight of a copper oxide (II) reagent, 1.0% by weight of DISPERBYK-2090 and 1.0% by weight of diethylene glycol distearate, and by stirring with an ultrasonic vibration device.

Comparative Example 6

A dispersion liquid was prepared by incorporating 0.05% by weight of a metallic silver reagent, 1.0% by weight of DISPERBK-2 and 1.0% by weight of diethylene distearate, and by stirring with an ultrasonic vibration device.

Comparative Example 7

A dispersion liquid was prepared in the same manner as in Example 1 except that 0.05% by weight of saccharin and 1.0% by weight of water were incorporated into the diethylene glycol.

Comparative Example 8

A powder of a copper oxide (I) reagent was pulverized with a jet mill, and this powder was mixed with nylon 6 particles having an average particle diameter of about 10 μm were mixed in a dry particle composing machine to prepare particles of the nylon 6 on which the copper oxide (I) was embedded in an exposed state. 0.05% by weight of the thus obtained particles were incorporated into butyl acetate, which was then stirred with an ultrasonic vibration device to obtain a dispersion liquid.

Table 1 shows whether the metallic copper fine particles (dispersion liquids) were produced Examples 1-9 and Comparative Examples 1-3.

<Identification of Metal Composition of Fine Particles>

The fine particles produced in Examples 1-9 and Comparative Example 3 were collected by filtration or the like, and the metal compositions were measured with an X-ray diffractometer manufactured by Rigaku Corporation. The results are shown in Table 1.

The measurement range is 2θ=30° to 60°. In the case of metallic copper, the peaks appear at the positions of 43° and 50°.

Figure 1:
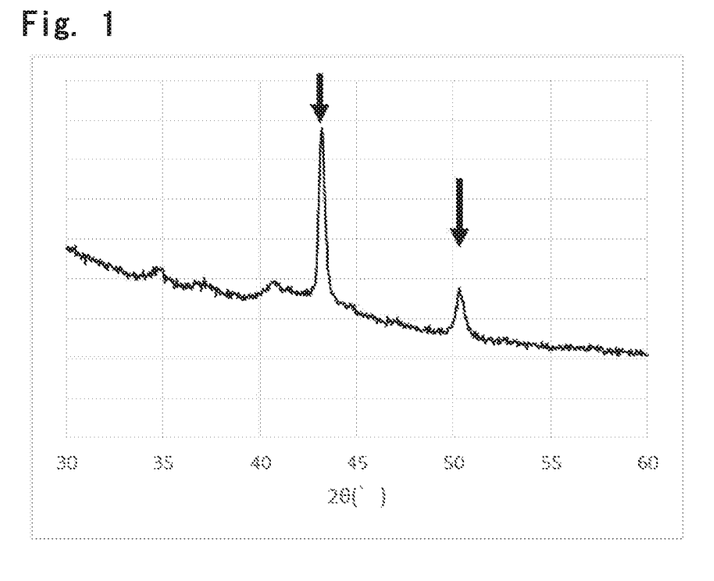
FIG. 1 an X-ray diffraction profile of particles in Example 1.

FIG. 1 shows a chart for the metallic copper fine particles produced in Example 1.

<Identification of Protective Layer of Fine Particles>

The fine particles produced in Examples 1-9 and Comparative Example 3 were collected by filtration or the like, and protective layers were identified with FT-IR manufactured by Agilent Technologies, Inc. The fine particles produced in Examples 1-9 and Comparative Example 3 had peaks in the range of about 1720 to 1730 $cm^{-1}$, which indicates that the ester compound is present as a protective layer for the fine particles.

Figure 2:
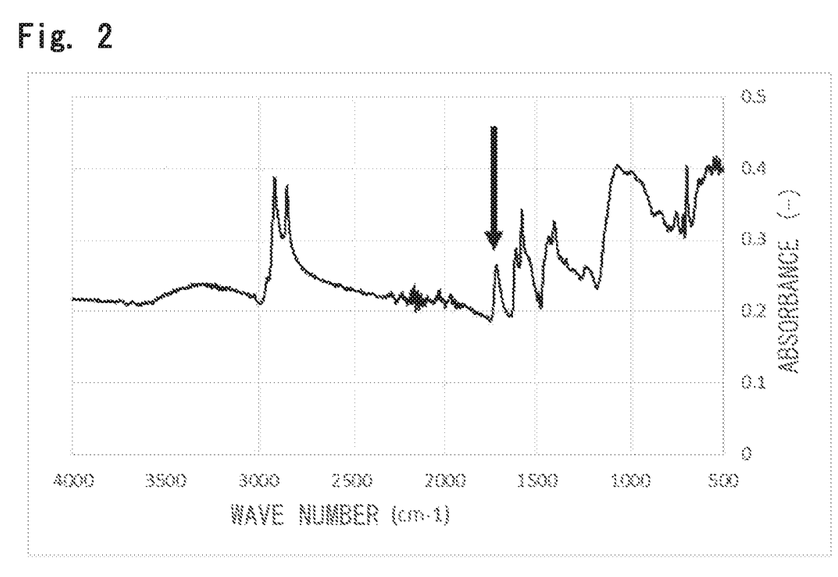
FIG. 2 an FT-IR chart of Example 1.

FIG. 2 shows a chart for the metallic copper fine particles produced in Example 1.

TABLE 1

| | Metallic copper fine particles (dispersion liquid) are produced? | Copper composition |
|---|---|---|
| Example 1 | Yes | Metallic copper |
| Example 2 | Yes | Metallic copper |
| Example 3 | Yes | Metallic copper |
| Example 4 | Yes | Metallic copper |
| Example 5 | Yes | Metallic copper |
| Example 6 | Yes | Metallic copper |
| Example 7 | Yes | Metallic copper |
| Example 8 | Yes | Metallic copper |

TABLE 1-continued

|  | Metallic copper fine particles (dispersion liquid) are produced? | Copper composition |
|---|---|---|
| Example 9 | Yes | Metallic copper |
| Comparative Example 1 | Not extractable | — |
| Comparative Example 2 | No particle formable | — |
| Comparative Example 3 | Yes | Metallic copper |

<Evaluation of Antiviral Activity>
(Method for Coating Dispersion Liquid on Nonwoven Fabric)

A dispersion liquid was prepared to contain a metallic ingredient at a concentration adjusted to be 0.05% by weight with respect to a binder resin. 90% by weight of the dispersion liquid, 9.9% by weight of photo-curable acrylic resin as the binder resin, and 0.1% by weight of photopolymerization initiator were mixed to form a coating liquid. An unprocessed nonwoven fabric was soaked in the coating liquid, which was then taken out and subjected to a roller squeezer to eliminate excess liquid. After that, the nonwoven fabric was dried for two minutes in a 90° C. dryer, and then, UV-irradiated for 10 minutes to produce a nonwoven fabric on which the metallic copper fine particles were fixed.

(Method of Evaluating Antiviral Activity of Nonwoven Fabric)

1. A virus suspension is prepared by infecting host cells with a virus, culturing, and then removing cell debris by centrifugation.
2. A test virus suspension is obtained by diluting the virus suspension of the above 1. 10 times with sterile distilled water.
3. 0.2 mL of the test virus suspension is inoculated on 0.4 g of a test piece of the nonwoven fabric.
4. After leaving at 25° C. for 2 hours, 20 mL of a SCDLP medium is added, which is then stirred with a vortex mixer to wash out the virus from the specimen.
5. The viral infectivity value is measured by a plaque measurement method and the antiviral activity value is calculated.
6. If the antiviral activity value is 3.0 or more, the antiviral activity against the virus can be determined as sufficient.

Table 2 shows the evaluation result on the antiviral activity for each of the nonwoven fabrics applied with the dispersion liquids prepared in Examples 1-9 and Comparative Examples 3-8, where the influenza virus and the feline calicivirus were used.

TABLE 2

|  | Antiviral activity value against influenza virus | Antiviral activity value against feline calicivirus |
|---|---|---|
| Example 1 | ≥4.7 | ≥4.7 |
| Example 2 | ≥4.7 | ≥4.7 |
| Example 3 | ≥4.7 | ≥4.7 |
| Example 4 | ≥4.7 | 4.2 |
| Example 5 | 4.5 | 3.8 |
| Example 6 | ≥4.7 | ≥4.7 |
| Example 7 | 4.6 | 3.9 |
| Example 8 | ≥4.7 | 4.3 |
| Example 9 | 4.5 | 3.7 |
| Comparative Example 3 | 1.2 | 0.3 |
| Comparative Example 4 | 1.0 | 0.5 |
| Comparative Example 5 | 0.3 | 0.1 |
| Comparative Example 6 | 0.8 | 0.1 |
| Comparative Example 7 | 3.5 | 0.6 |
| Comparative Example 8 | 3.4 | 0.2 |

INDUSTRIAL APPLICABILITY

The metallic copper fine particles of the present invention are provided in the form of dispersion liquid and contained as a diluent in a resin composition to constitute textiles or the like, or the dispersion liquid may be directly coated on or impregnated in textiles or the like, so that it is possible to impart antiviral activity to the textiles such as face masks, wet wipes, air conditioner filters, air purifier filters, clothes, work clothes, curtains, carpets, automotive parts, sheets, towels, and, cleaning supplies like wipes.

Further, a low-boiling point solvent may be used as a dispersion medium of the dispersion liquid, so that the dispersion liquid can be used as the diluent for the coating composition or the resin composition, thereby imparting antiviral activity to the coating or the resin article.

Furthermore, the metallic copper fine particles can be used for medical devices, medical device-packaging films, waste containers, garbage bags, wall materials and flooring of public facilities such as nursing homes, hospitals and schools, wax coating materials, and tools for disposing vomit and excreta.

Application is not limited to sanitary products, but the present invention can be applied to various products such as electrically conductive films, films, metal sheets, glass sheets, marine paints, heat exchanger fins and the like.

The invention claimed is:

1. Metallic copper fine particles, which are coated with a fatty acid and an ester compound, wherein
    the ester compound is an ester compound of the fatty acid and polyol, and
    the polyol is selected from the group consisting of ethylene glycol, diethylene glycol, and triethylene glycol.
2. The metallic copper fine particles according to claim 1, wherein the fatty acid is a higher fatty acid having a carbon number of 10 to 22.
3. The metallic copper fine particles according to claim 1, having an average particle diameter in a range of 10 to 500 nm.
4. An antiviral agent containing the metallic copper fine particles according to claim 1.
5. The antiviral agent according to claim 4, including a dispersion liquid containing the metallic copper fine particles dispersed in a solvent.
6. The antiviral agent according to claim 4, including a resin composition containing the metallic copper fine particles dispersed in a resin.
7. The antiviral agent according to claim 4, containing the metallic copper fine particles in an amount of 0.05 to 2.0% by weight and having an antiviral activity value of not lower than 3.0.
8. The antiviral agent according to claim 4, containing the metallic copper fine particles in an amount of 0.05 to 2.0% by weight in terms of metallic copper so as to generate superoxide anion radical in an amount of not less than 5000 counts/mL by a reaction with MPEC when the amount of the radical is expressed as a luminescence amount by chemiluminescence.

9. The antiviral agent according to claim 4, wherein the antiviral agent containing metallic copper fine particles has a protein decrease rate of not less than 10% in a measurement by the BSA method.

10. A method for producing the metallic copper fine particles according to claim 1, including:
introducing fatty acid copper into polyol and heat-mixing to prepare a dispersion liquid containing metallic copper fine particles coated at least with the fatty acid;
mixing the dispersion liquid with a low-boiling point solvent that contains a dispersing agent and an ester compound; and
separating the polyol and the low-boiling point solvent into two phases and extracting the metallic copper fine particles coated with the fatty acid and the ester compound from the polyol into the low-boiling point solvent,
wherein the ester compound is an ester compound of the fatty acid and polyol, and
the polyol is selected from the group consisting of ethylene glycol, diethylene glycol and triethylene glycol.

11. The method for producing metallic copper fine particles according to claim 10, wherein the low-boiling point solvent containing the extracted metallic copper fine particles is volatilized.

12. The method for producing metallic copper fine particles according to claim 10, wherein the low-boiling point solvent is selected from the group consisting of butyl acetate, ethyl acetate, and methyl isobutyl ketone.

13. A method for producing the metallic fine particles according to claim 1, including:
introducing a fatty acid and a copper compound into polyol and heat-mixing to prepare a dispersion liquid containing metallic copper fine particles coated at least with the fatty acid;
mixing the dispersion liquid with a low-boiling point solvent that contains a dispersing agent and an ester compound; and
separating the polyol and the low-boiling point solvent into two phases and extracting the metallic copper fine particles coated with the fatty acid and the ester compound from the polyol into the low-boiling point solvent,
wherein the ester compound is an ester compound of the fatty acid and polyol, and
the polyol is selected from the group consisting of ethylene glycol, diethylene glycol and triethylene glycol.

14. The method for producing metallic copper fine particles according to claim 13, wherein the copper compound is selected from the group consisting of copper acetate, copper chloride, and copper bromide.

15. A method for producing the metallic fine particles according to claim 1, including:
incorporating fatty acid copper into polyol and heating at a temperature lower than the thermal decomposition starting temperature of the fatty acid copper so as to form the metallic copper fine particles in the polyol.

* * * * *